(12) United States Patent
Vidulich et al.

(10) Patent No.: US 12,339,227 B2
(45) Date of Patent: Jun. 24, 2025

(54) MODULAR PHOTOELECTRIC SMOKE SENSOR TUBE

(71) Applicant: Carrier Corporation, Palm Beach Gardens, FL (US)

(72) Inventors: Joseph Anthony Vidulich, Englewood, FL (US); Dennis Michael Gadonniex, Bradenton, FL (US)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 148 days.

(21) Appl. No.: 17/118,095

(22) Filed: Dec. 10, 2020

(65) Prior Publication Data

US 2022/0050053 A1 Feb. 17, 2022

Related U.S. Application Data

(60) Provisional application No. 63/066,503, filed on Aug. 17, 2020.

(51) Int. Cl.
| | | |
|---|---|---|
| *G01N 21/47* | (2006.01) | |
| *B08B 5/02* | (2006.01) | |
| *G01N 21/85* | (2006.01) | |
| *G01N 33/00* | (2006.01) | |

(52) U.S. Cl.
CPC ............ *G01N 21/47* (2013.01); *G01N 21/85* (2013.01); *G01N 33/0036* (2013.01); *G01N 2021/8578* (2013.01)

(58) Field of Classification Search
CPC .... G01N 21/47; G01N 21/85; G01N 33/0036; G01N 2021/8578; G08B 17/107; B08B 5/04; B08B 5/02

See application file for complete search history.

(56) References Cited

U.S. PATENT DOCUMENTS

| | | | |
|---|---|---|---|
| 4,758,827 A | 7/1988 | Powers | |
| 5,844,148 A | 12/1998 | Klein et al. | |
| 5,898,377 A * | 4/1999 | Adachi ................. | G08B 29/18 340/630 |
| 6,085,576 A | 7/2000 | Sunshine et al. | |

(Continued)

FOREIGN PATENT DOCUMENTS

| | | |
|---|---|---|
| CN | 1305100 A | 7/2001 |
| CN | 201145935 | 11/2008 |

(Continued)

OTHER PUBLICATIONS

European Search Report for Application No. 20214692.4; Issued Jun. 9, 2021; 10 Pages.

(Continued)

*Primary Examiner* — Peter J Macchiarolo
*Assistant Examiner* — Anthony W Megna Fuentes
(74) *Attorney, Agent, or Firm* — CANTOR COLBURN LLP

(57) ABSTRACT

A smoke detector for an air duct includes a photoelectric detection system and a sampling space in fluid communication with the air duct wherein the sampling space is enclosed by a removable sampling space enclosure having an optic window, and the photoelectric detection system is located adjacent to the optic window. The sampling space enclosure can be removed or replaced without removing or replacing the entire smoke detector.

19 Claims, 3 Drawing Sheets

(56) References Cited

U.S. PATENT DOCUMENTS

| | | | |
|---|---|---|---|
| 6,288,647 B1* | 9/2001 | Yamano | G08B 17/107 340/630 |
| 6,521,907 B1* | 2/2003 | Shoaff | G08B 17/107 356/628 |
| 6,741,181 B2 | 5/2004 | Skaggs | |
| 7,062,953 B2 | 6/2006 | Yamano et al. | |
| 7,129,847 B2 | 10/2006 | Right et al. | |
| 7,958,794 B2 | 6/2011 | Sahibzada et al. | |
| 8,141,422 B2 | 3/2012 | Hall et al. | |
| 8,266,974 B2 | 9/2012 | Hall et al. | |
| 8,373,858 B2 | 2/2013 | Fergenson | |
| 8,646,305 B2 | 2/2014 | Townsend et al. | |
| 8,797,531 B2 | 8/2014 | Knox et al. | |
| 8,934,101 B2 | 1/2015 | Ido et al. | |
| 8,939,013 B2 | 1/2015 | Brighenti et al. | |
| 9,032,780 B2 | 5/2015 | Anderson et al. | |
| 9,239,291 B2 | 1/2016 | Sakamoto | |
| 9,459,208 B2 | 10/2016 | Orsini et al. | |
| 9,500,584 B2 | 11/2016 | Neijzen et al. | |
| 9,746,363 B2 | 8/2017 | Ajay et al. | |
| 9,772,278 B2 | 9/2017 | Han | |
| 9,940,806 B2 | 4/2018 | Al-Farra et al. | |
| 10,078,948 B2* | 9/2018 | Bressanutti | G08B 17/107 |
| 10,161,857 B2 | 12/2018 | Nomoto | |
| 10,267,711 B2 | 4/2019 | Williamson | |
| 2005/0134468 A1 | 6/2005 | Thomas et al. | |
| 2014/0160473 A1* | 6/2014 | McKendree | G01N 21/532 356/244 |
| 2014/0168647 A1* | 6/2014 | Ju | G08B 17/107 29/527.1 |
| 2015/0103346 A1* | 4/2015 | Erdtmann | G08B 17/107 356/338 |
| 2015/0254953 A1 | 9/2015 | Gandara et al. | |
| 2017/0213434 A1 | 7/2017 | Bressanutti et al. | |
| 2018/0178259 A1* | 6/2018 | Gillies | H04N 5/2257 |
| 2018/0322753 A1* | 11/2018 | Stibich | G08B 17/10 |
| 2020/0152034 A1* | 5/2020 | Duric | H01L 33/50 |

FOREIGN PATENT DOCUMENTS

| | | | | |
|---|---|---|---|---|
| CN | 101763708 A | | 6/2010 | |
| CN | 105008894 A | | 10/2015 | |
| CN | 105225401 A | | 1/2016 | |
| EP | 1975896 B1 | | 5/2010 | |
| GB | 2347541 A | | 9/2000 | |
| JP | H09270084 A | | 10/1997 | |
| JP | 3638261 B2 | | 4/2005 | |
| KR | 20120037049 A | * | 4/2012 | B63J 2/02 |

OTHER PUBLICATIONS

TFDA-DUCT—Analysis Chamber; Tecnofire Detection; retrieved Sep. 5, 2019, 2 pages.
Thompson IV, Duct Smoke Detectors, Conklin Metal Industries Sheet Metal, Duct Fab & HVAC Supplies, Mar. 26, 2019, 10 pages.
Ventilation Control Products Sweden AB; ventilationcontrolproducts.net. retrieved Sep. 5, 2019, 4 pages.
EP Application No. 20214692.4, Search Report, Jun. 9, 2021, 10 pages.
Chinese Office Action for Application No. 202011549168.X, Issued Jul. 23, 2024, 11 Pages.
Wu et al. "Fire Detection and Control Engineering" ,2nd Edition, University of Science and Technology of China Press, Sep. 1, 2013. English Abstract Provided.

\* cited by examiner

MODULAR PHOTOELECTRIC SMOKE SENSOR TUBE

CROSS-REFERENCE TO RELATED APPLICATIONS

This application claims the benefit of U.S. Provisional Application No. 63/066,503, filed Aug. 17, 2020, the disclosure of which is incorporated herein by reference in its entirety.

BACKGROUND

The embodiments disclosed herein relate to smoke detectors and, more particularly, to photoelectric smoke detectors for air ducts.

A smoke detector is a device that detects smoke and issues an alarm. A photoelectric smoke detector is a type of smoke detector that works based on light reflection principals and generally includes a light emitter, a light receiver and an optic chamber. When there is no smoke in the optic chamber and the optic chamber is empty or mostly empty, the light receiver typically receives a small amount of light reflected from chamber surfaces. On the other hand, when smoke is present in the optic chamber, the light receiver receives more light due to that light being reflected from the smoke particles. When an amount of the received light exceeds a threshold level, an alarm is triggered.

Detectors for sensing one or more conditions within a duct of a heating, ventilation, and air conditioning system are typically mounted to a flange or other component and/or the outside of an air duct and include a sampling pipe which extends laterally into the duct from the exterior. The air within the duct flows into inlets formed in the sampling pipe to a smoke sensor, located in a housing outside of the duct. The air is then returned to the interior of the duct via an output flow pipe.

Dust and debris may accumulate within the smoke detector resulting in false alarms and frequent maintenance. Maintenance of a duct detector is typically a time consuming procedure having limited effectiveness. As a result, maintenance of a duct detector often entails replacement of the detector.

BRIEF DESCRIPTION

According to an embodiment, a smoke detector for an air duct includes a sampling space in fluid communication with the air duct and a photoelectric detection system wherein the sampling space is enclosed by a removable sampling space enclosure having an optic window, and the photoelectric detection system is located adjacent to the optic window.

In addition to one or more of the features described above, or as an alternative, in further embodiments the removable sampling space enclosure includes an electrically conductive material.

In addition to one or more of the features described above, or as an alternative, in further embodiments the removable sampling space enclosure absorbs infrared light.

In addition to one or more of the features described above, or as an alternative, in further embodiments the photoelectric detection system includes at least one light emitter and at least one light receiver. The at least one light receiver may receive light at different angles.

In addition to one or more of the features described above, or as an alternative, in further embodiments the at least one light emitter emits multiple wavelengths.

In addition to one or more of the features described above, or as an alternative, in further embodiments the smoke detector includes a light mold. The light mold may form a portion of the sampling space enclosure.

In addition to one or more of the features described above, or as an alternative, in further embodiments the removable sampling space enclosure includes a cleaning port.

In addition to one or more of the features described above, or as an alternative, in further embodiments the optic window has anti-static or hydrophobic properties.

According to another embodiment, a method for detecting smoke in an air duct includes emitting light into a removable sampling space enclosure, receiving light from the sampling space enclosure at multiple angles using a photoelectric detection system, and comparing the emitted light to the received light. The sampling space enclosure includes an optic window and encloses a sampling space in fluid communication with the air duct. The photoelectric detection system includes at least one light emitter and at least one light receiver and is located adjacent to the optic window and the photoelectric detection system is positioned to emit light into the sampling space and receive light from the sampling space.

In addition to one or more of the features described above, or as an alternative, in further embodiments the photoelectric detection system includes multiple light receivers configured to receive light at different angles.

According to another embodiment, a method of maintaining a smoke detector for an air duct includes cleaning or replacing at least one portion of a sampling space enclosure, wherein the sampling space enclosure encloses a sampling space in fluid communication with the air duct and the smoke detector comprises a photoelectric detection system located adjacent to an optic window of the sampling space enclosure.

In addition to one or more of the features described above, or as an alternative, in further embodiments the sampling space enclosure comprises a cleaning port and cleaning comprises applying compressed air or suction through the cleaning port.

In addition to one or more of the features described above, or as an alternative, in further embodiments cleaning comprises removing at least a portion of the sampling space enclosure from the smoke detector and removing contaminants from the sampling space enclosure and the optic window.

In addition to one or more of the features described above, or as an alternative, in further embodiments the sampling space enclosure has at least two portions and cleaning comprises removing one portion to provide access to the interior of the sampling space enclosure.

In addition to one or more of the features described above, or as an alternative, in further embodiments wherein the sampling space enclosure has at least two portions and replacing the sampling space enclosure comprises replacing one or more portions of the sampling space enclosure.

In addition to one or more of the features described above, or as an alternative, in further embodiments the sampling space enclosure comprises a first portion, a second portion, a light mold and an optic window and replacing the sampling space enclosure comprises replacing the first portion, the second portion or both.

In addition to one or more of the features described above, or as an alternative, in further embodiments further comprising cleaning the light mold, the optic window or both.

BRIEF DESCRIPTION OF THE DRAWINGS

The following descriptions should not be considered limiting in any way. With reference to the accompanying drawings, like elements are numbered alike.

DETAILED DESCRIPTION

A smoke detector for an air duct includes a sampling space in fluid communication with the air duct and a photoelectric detection system. The sampling space is enclosed by a sampling space enclosure having an optic window. The photoelectric detection system includes at least one light emitter and at least one light receiver. The at least one light emitter and at least one light receiver are located adjacent to the optic window. The sampling space enclosure is removable and can either be cleaned or replaced as needed, without replacing the entire smoke detector. The ability to clean and/or replace the sampling space enclosure helps to decrease the number of false positives due to dust and other accumulated materials as well as maintains the sensitivity of the smoke detector.

A detailed description of one or more embodiments of the disclosed apparatus and method are presented herein by way of exemplification and not limitation with reference to the Figures.

Figure 1:
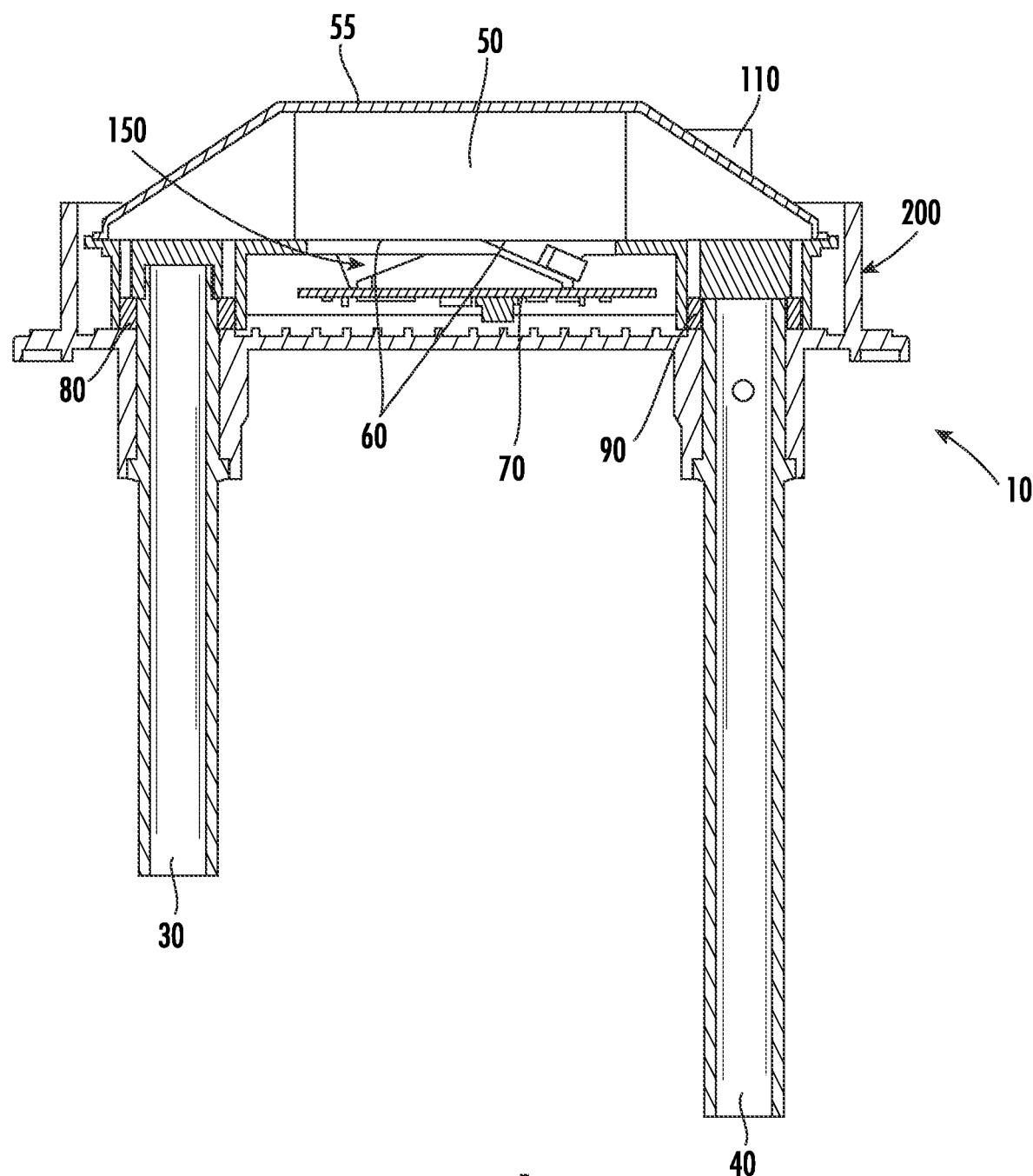
FIG. 1 is a cross section of an exemplary smoke detector.

FIG. 1 shows a smoke detector 10. The smoke detector includes an inlet 30, an outlet 40 and a sampling space 50. The sampling space 50 is enclosed by a removable sampling space enclosure 55. The removable sampling space enclosure 55 has one or more optic windows 60 and may include a light mold 150. The removable sampling space enclosure 55 may include an optional cleaning port 110. The cleaning port allows for use of a suction device, compressed air or a combination thereof for cleaning the removable sampling space enclosure 55, by, for example, using air to force through the sampling space enclosure 55 dust or other accumulating materials that may cause obscuration of light in the sampling space enclosure 55. The photoelectric detection system 70 is located adjacent to the optic window 60. The sampling space 50 is in fluid communication with the air duct (not shown). As air moves through the air duct a portion of the air enters the inlet 30 and moves through the sampling space 50, and exits through the outlet 40, rejoining the air transiting the duct.

The removable sampling space enclosure may be unitary or may have more than one portion. At least a portion of the removable sampling space enclosure 55 may be removed for cleaning or replacement without replacing the entire smoke detector 10, or any of the other elements of the detector 10. The ability to remove at least a portion of the removable sampling space enclosure 55 and leave the remainder of the system in place facilitates maintenance, reduces false positives due to dust or other accumulating materials, and is cost effective. In some embodiments one or more of the light mold 150 and the optic window(s) 60 can be separated from the removable sampling space enclosure 55. This modularity allows inspection, evaluation and maintenance/replacement of each element as required.

The sampling space enclosure 55 has receiving ends 80 and 90 which facilitate the removal and replacement of the sampling space enclosure 55. The receiving ends 80, 90 may include a gasket or other type of seal. Alternatively a gasket or seal may be located on each end of an installation mount 200 or the inlet 30 and outlet 40.

The removable sampling space enclosure 55 may absorb infrared light and may be made of infrared absorbing material or may be coated with an infrared absorbing coating. In some embodiments the sampling space enclosure 55 comprises an electrically conductive material that includes IR absorbing material. The sampling space enclosure 55 includes one or more optic windows 60 to enable detection and optionally measurement of smoke and other materials. The optic window 60 transmits greater than or equal to 90% of the light transmitted by the detection system for effective detection and/or measurement and may be made of a polymer, glass or other suitable material. The optic window 60 may exhibit anti-static and/or super hydrophobic properties in the form of a coating which can facilitate cleaning of the optic window, sampling space enclosure or both. The anti-static and/or super hydrophobic properties can also reduce the possibility of particles remaining on the optic window and interfering with detection, measurement or both. The sampling space 50 may have any shape that does not interfere with the detection system 10. Exemplary cross sectional shapes include circular, square, and rectangular.

Figure 2:
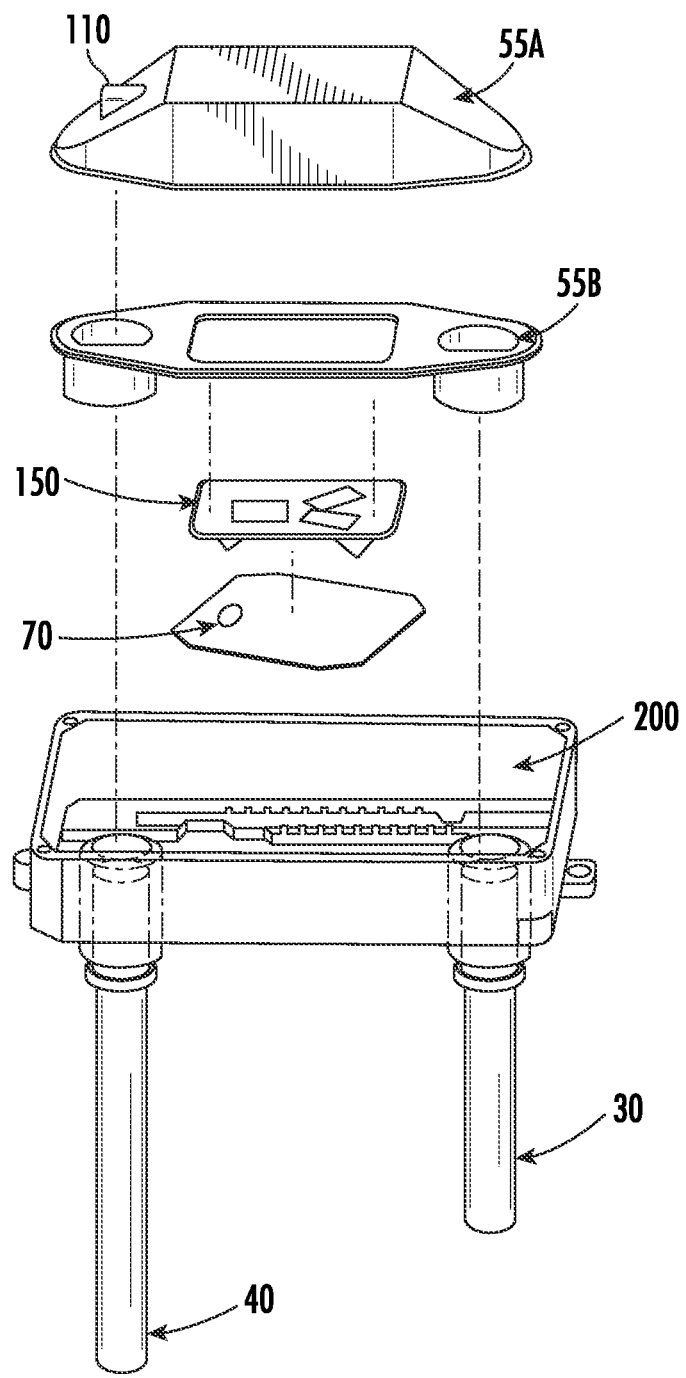
FIG. 2 is an exploded view of an exemplary smoke detector.

FIG. 2 is an exploded view of an embodiment of the smoke detector 10 showing the inlet 30 and outlet 40, and a mounting element 200. In this exemplary embodiment the removable sampling space enclosure includes at least two portions shown here as a first portion of the removable sampling space enclosure 55a and a second portion of the removable sampling space enclosure 55b. Also shown are optic windows 60, photoelectric detection system 70, and light mold 150.

The photoelectric detection system 70 is located adjacent to the optic window 60. The photoelectric detection system 70 uses light to evaluate a volume (in this example, the volume of air within the sampling space 50) for the presence of a condition such as a fire or other hazard. In this specification, the term "light" means coherent or incoherent radiation at any frequency or a combination of frequencies in the electromagnetic spectrum. In an example, the photoelectric detection system 70 uses light scattering to determine the presence of particles in the sampling space to indicate the existence of a threshold condition or event. In this specification, the term "scattered light" may include any change to the amplitude/intensity or direction of the incident light, including reflection, refraction, diffraction, absorption, and scattering in any/all directions. In this example, light is emitted through the optic window 60 into the sampling space 50; when the light encounters an object suspended (i.e. floating) within the surrounding medium (air) (a smoke particle or gas molecule for example), the light will be scattered and/or absorbed due to a difference in the refractive index of the object compared to the surrounding medium (air). Depending on the object, the light can be scattered in all different directions. Detecting light scattered by an object can provide information about the sampling space including determining the presence of a threshold condition or event.

Light scattering is a physical property attributed to the interaction of light with the atoms or surface that make up the material. The angle of redirection for light emitted from a source is dependent on the material composition and geometry. The redirection of light can be isotropic, where every angle receives the same quantity of radiation. In addition, the redirection of light can be anisotropic or the redirection of a quantity of light non-uniformly with respect to angle. The amount of anisotropy is dependent on the optical and electronic properties combined with geometric properties of the material. The anisotropy is also frequency dependent. In practice this principle can be utilized for discriminating one material from another material; a group of materials from another group of materials; or combinations of materials and groups of materials.

The photoelectric detection system 70 includes at least one light emitter and at least one light receiver. The at least one emitter may be capable of emitting multiple wavelengths. The at least one receiver may be capable of detecting (receiving) multiple wavelengths. The ability to emit and detect multiple wavelengths facilitates in distinguishing different types of materials in the sampling space. The emitter and receiver may include fiber optic cables, laser diodes, photodiodes, or other types of light production and reception.

Figure 3:
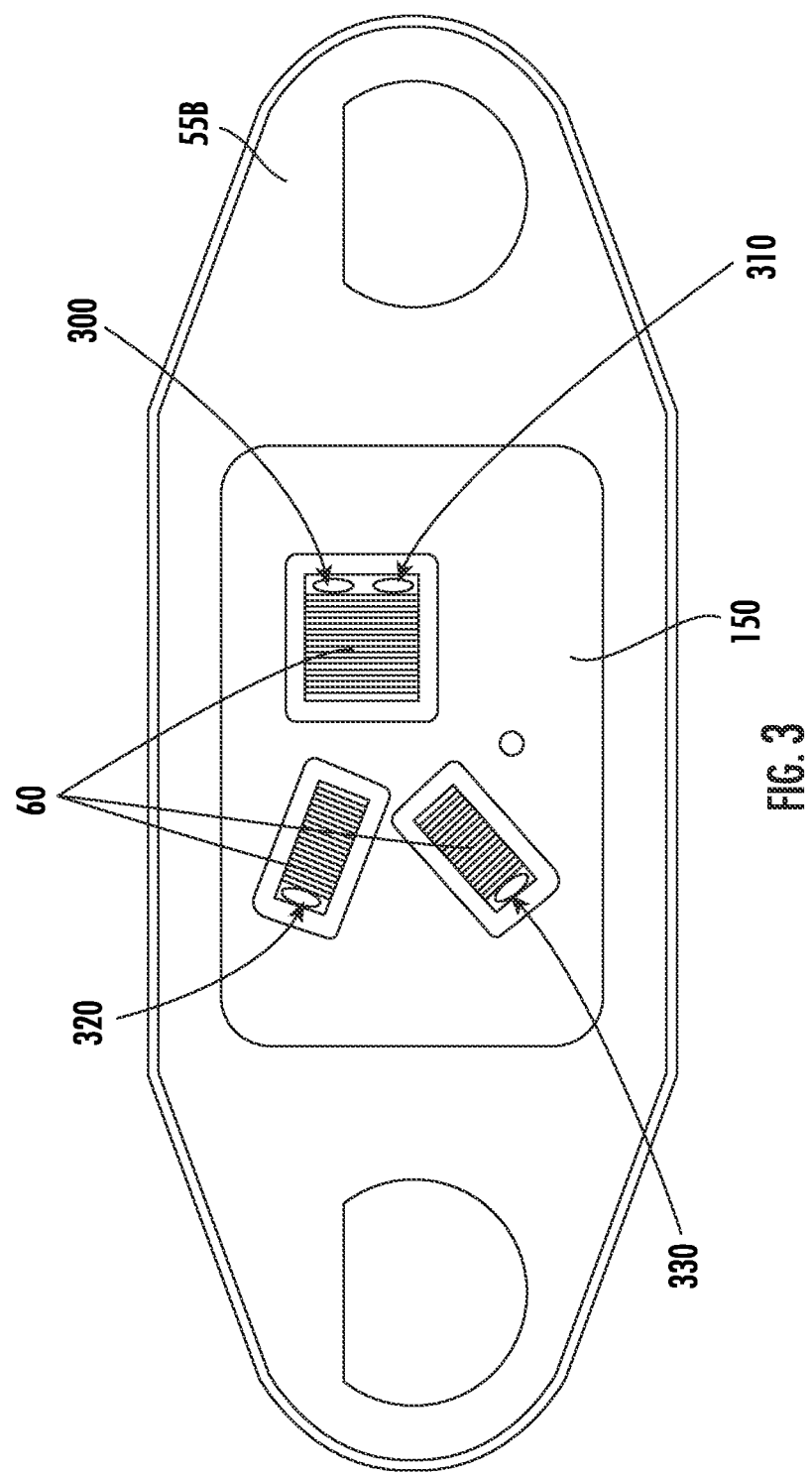
FIG. 3 is a top view of an exemplary smoke detector.

The light from the emitter is transmitted through the optic window 60 into the sampling space 50. An exemplary arrangement of emitters and receiver is shown in FIG. 3. A first infrared emitter 300, a blue light emitter 310, a second infrared emitter 320, and a receiver 330 are located adjacent to the optic windows 60 and light mold 150.

The light interacts with any particles present in the sampling space enclosure 50 and is reflected or transmitted back to the receiver. A comparison of the light provided by the emitter and/or changes to the light reflected back to the receiver will indicate whether or not changes in the atmosphere are present in the sampling space 50 that are causing the scattering of the light. The scattered light as described herein is intended to additionally include reflected, transmitted, and absorbed light. Although the detection system is described as using light scattering to determine a condition or event, embodiments where light obscuration, absorption, and fluorescence is used in addition to or in place of light scattering are also within the scope of the disclosure.

In some embodiments, light from the photoelectric detection system 70 passes through a light mold, guide, lens or other distribution device, for convenience characterized here as a "light mold" 150. The light mold enables collection of light from multiple angles. The light mold can be fabricated from any suitable material, including but not limited to, fiber optics, free space optics, molded plastic optics or photonic integrated circuits for example. In addition, the light mold and the emitter, receiver or both may be integrated.

The photoelectric detection system 70 may be used to distinguish smoke from other types of hazardous conditions or nuisances. Each emitter is associated with one or more receivers for collecting/receiving scattered light from the sampling space 50. Each of the one or more of receivers is oriented at a different angle relative to the emitter. For example, a first angle is formed between the emitter and the first receiver, and a second angle is formed between the emitter and the second receiver. The first angle and the second angle are known and are distinct. In some embodiments, the different angles can be achieved by physically orienting/positioning the receivers differently. In other embodiments, the different angles can be achieved by using a plurality of emitters. In other embodiments, a light mold can be used to receive scattered light from different scattering angles at the one or more receivers. The light mold can be operably connected to and configured to support the emitter and the plurality of receivers such that the plurality of receivers each receive scattered light from a desired angle.

The photoelectric detection system may include a control system (not shown). The control system may be utilized to manage the detection system operation and may include control of components, data acquisition, data processing and data analysis. In some embodiments the detection system may include other components to detect other conditions such as air quality. The control system includes a processor and memory. Exemplary processors include microprocessors, system on a chip (SOC), field programmable gate array (FGPA), and the like. The processor may be coupled to the at least one light emitter and the at least one light receiver. The at least one light receiver is configured to convert the received scattered light into a corresponding signal receivable by the processor. The signal outputs may be compared by the processor to the signal from the emitted light to determine whether a threshold condition is present.

In addition to being operably coupled to the at least one emitter and to the at least one receiver, the control system may be associated with one or more input/output devices. In an embodiment, the input/output devices may include an alarm or other signal, or a fire suppression system which are activated upon detection of a predefined event or condition. It should be understood herein that the term alarm, as used herein, may indicate any of the possible outcomes of a detection.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A smoke detector for an air duct comprises a sampling space in fluid communication with the air duct and a photoelectric detection system, wherein the sampling space is enclosed by a removable sampling space enclosure having an optic window, wherein the photoelectric detection system is separated from the removable sampling space enclosure by the optic window; and wherein the photoelectric detection system comprises at least one light emitter and at least one light receiver, wherein the at least one light receiver receives light at different angles from the at least one light emitter.

2. The smoke detector of claim 1, wherein the removable sampling space enclosure comprises an electrically conductive material.

3. The smoke detector of claim 1, wherein the removable sampling space enclosure absorbs infrared light.

4. The smoke detector of claim 1, wherein the photoelectric detection system is located on one side of the removable sampling space enclosure.

5. The smoke detector of claim 4, wherein the at least one light emitter emits multiple wavelengths.

6. The smoke detector of claim 1, further comprising a light mold.

7. The smoke detector of claim 6, wherein the light mold forms a portion of the removable sampling space enclosure.

8. The smoke detector of claim 1, wherein the removable sampling space enclosure further comprises a cleaning port.

9. The smoke detector of claim 1, wherein the optic window has anti-static or hydrophobic properties.

10. The smoke detector of claim 1, wherein the removable sampling space enclosure comprises two portions.

11. A method for detecting smoke in an air duct comprising emitting light into a removable sampling space enclosure, receiving light from the removable sampling space enclosure at multiple angles using a photoelectric detection system, and comparing the emitted light to the received light, wherein the removable sampling space enclosure comprises an optic window and encloses a sampling space in fluid communication with the air duct, and wherein the photoelectric detection system comprises at least one light emitter and at least one light receiver, and is separated from the removable sampling space enclosure by the optic window.

12. The method of claim 11, wherein the photoelectric detection system comprises multiple light receivers configured to receive light at different angles and the photoelectric detection system is located on one side of the removable sampling space enclosure.

13. A method of maintaining a smoke detector for an air duct, comprising cleaning or replacing at least one portion of a removable sampling space enclosure, wherein the removable sampling space enclosure encloses a sampling space in fluid communication with the air duct and the smoke detector comprises a photoelectric detection system separated from the removable sampling space enclosure by an optic window of the removable sampling space enclosure; wherein the photoelectric detection system further comprises at least one light emitter and at least one light receiver, and where the at least one light receiver receives light at different angles from the at least one light emitter.

14. The method of claim 13, wherein the removable sampling space enclosure comprises a cleaning port and cleaning comprises applying compressed air or suction through the cleaning port.

15. The method of claim 13, wherein cleaning comprises removing at least a portion of the removable sampling space enclosure from the smoke detector and removing contaminants from the removable sampling space enclosure and the optic window, wherein at least the portion of the removable sampling space is removable without removing the photoelectric detection system.

16. The method of claim 13, wherein the removable sampling space enclosure has at least two portions and cleaning comprises removing one portion to provide access to the interior of the removable sampling space enclosure.

17. The method of claim 13, wherein the removable sampling space enclosure has at least two portions and replacing the removable sampling space enclosure comprises replacing one or more portions of the removable sampling space enclosure.

18. The method of claim 17, wherein the removable sampling space enclosure comprises a first portion, a second portion, a light mold, and the optic window and replacing the removable sampling space enclosure comprises replacing the first portion, the second portion, or both.

19. The method of claim 18, further comprising cleaning the light mold, the optic window or both.

* * * * *